United States Patent
Deguchi et al.

(10) Patent No.: US 9,499,415 B2
(45) Date of Patent: Nov. 22, 2016

(54) ULTRAVIOLET IRRADIATION APPARATUS

(71) Applicant: CHIYODA KOHAN CO., LTD., Tokyo (JP)

(72) Inventors: Kenichiro Deguchi, Tokyo (JP); Hiroshi Nakagaki, Tokyo (JP); Satoshi Yamaguchi, Tokyo (JP); Takashi Fujii, Tokyo (JP)

(73) Assignee: CHIYODA KOHAN CO., LTD, Tokyo (JP)

( * ) Notice: Subject to any disclaimer, the term of this patent is extended or adjusted under 35 U.S.C. 154(b) by 0 days.

(21) Appl. No.: 14/459,908

(22) Filed: Aug. 14, 2014

(65) Prior Publication Data
US 2016/0046507 A1 Feb. 18, 2016

(51) Int. Cl.
*C02F 1/32* (2006.01)
*G01J 1/42* (2006.01)
*A61L 2/10* (2006.01)

(52) U.S. Cl.
CPC ............. *C02F 1/325* (2013.01); *G01J 1/429* (2013.01); *A61L 2/10* (2013.01); *C02F 2201/326* (2013.01); *C02F 2201/3227* (2013.01); *C02F 2201/3228* (2013.01); *C02F 2301/026* (2013.01)

(58) Field of Classification Search
CPC ....... A61L 2/10; B01J 19/123; B01J 19/243; B01J 19/2415
USPC .................................................. 250/432 R
See application file for complete search history.

(56) References Cited

U.S. PATENT DOCUMENTS

| | | | | |
|---|---|---|---|---|
| 5,997,812 A | * | 12/1999 | Burnham et al. | 422/24 |
| 6,083,387 A | * | 7/2000 | LeBlanc et al. | 210/199 |
| 2003/0052278 A1 | * | 3/2003 | Duarte | 250/438 |
| 2004/0004044 A1 | * | 1/2004 | Anderson | C02F 1/325 210/748.11 |
| 2006/0219630 A1 | * | 10/2006 | Abe et al. | 210/600 |
| 2008/0164422 A1 | * | 7/2008 | Kim | A61L 2/0011 250/429 |

(Continued)

FOREIGN PATENT DOCUMENTS

| | | |
|---|---|---|
| JP | S57-113884 A | 7/1982 |
| JP | S63-166489 A | 7/1988 |

(Continued)

OTHER PUBLICATIONS

Nov. 11, 2015 Office Action issued in Japanese Application No. 2012-023000.

(Continued)

*Primary Examiner* — Jack Berman
*Assistant Examiner* — Kevin Chung
(74) *Attorney, Agent, or Firm* — Oliff PLC (57) ABSTRACT

An ultraviolet irradiation device that is used for a fluid to be irradiated having a low ultraviolet ray transmissivity, a spirally wound tube in which the fluid to be irradiated flows is supported and fixed, and an irradiation amount of ultraviolet rays with which the fluid is irradiated is increased. A tube 3 having ultraviolet ray transmitting property is spirally wound on an outer circumferential surface of a support pipe 5, a plurality of ultraviolet lamps 7 are disposed around an axis of the support pipe apart from the tube, an inner case 9 that supports the support pipe and that encloses the plurality of ultraviolet lamps is provided, and a fluid flows in the tube and is irradiated with ultraviolet rays. The tube which is a fluid channel is thereby fixed to the support pipe, so that breakage of the tube and the ultraviolet lamps 7 can be prevented.

12 Claims, 8 Drawing Sheets

(56) References Cited

U.S. PATENT DOCUMENTS

| | | | |
|---|---|---|---|
| 2008/0224066 A1* | 9/2008 | Nolen et al. | 250/436 |
| 2010/0326114 A1* | 12/2010 | Kim | C02F 1/325 62/264 |
| 2016/0009570 A1* | 1/2016 | Yu | C02F 1/325 210/748.1 |

FOREIGN PATENT DOCUMENTS

| | | | |
|---|---|---|---|
| JP | H05-253565 A | 10/1993 | |
| JP | H08-266889 A | 10/1996 | |
| JP | H10-113657 A | 5/1998 | |
| JP | A-2004-66045 | 3/2004 | |
| JP | 2006-514852 A | 5/2006 | |
| WO | 2010/091815 A1 | 8/2010 | |
| WO | WO 2014/113917 A1 * | 7/2014 | C02F 1/32 |

OTHER PUBLICATIONS

Jul. 5, 2016 Office Action issued in Japanese Application No. 2012-023000.

* cited by examiner

ULTRAVIOLET IRRADIATION APPARATUS

BACKGROUND OF THE INVENTION

Field of the Invention

The present invention relates to an ultraviolet irradiation device, and particularly relates to an ultraviolet irradiation device that irradiates ultraviolet rays from outside a tube in which a fluid flows.

Description of the Related Art

There is known an ultraviolet irradiation device for use in inactivation of bacteria and viruses in a fluid, decomposition of harmful substances in a fluid and the like by irradiating the fluid with ultraviolet rays.

For example, Patent Literature 1 discloses an ultraviolet irradiation device of an external irradiation type. In this device, a tube having an ultraviolet ray transmitting property is spirally wound and is disposed in a casing, ultraviolet lamps are disposed inside the spiral, and the fluid which flows in the tube is irradiated with ultraviolet rays from outside the tube. Patent Literature 1 discloses that when the tube of polytetrafluoroethylene with a high ultraviolet ray transmissivity is spirally disposed, some of the ultraviolet rays irradiated by the ultraviolet lamps are directly absorbed by the fluid to be irradiated in the tube which is spirally wound, whereas a remainder is repeatedly reflected in gaps in the tube and gradually absorbed by the fluid, and that the utilization efficiency of ultraviolet rays can be, therefore, improved. The ultraviolet irradiation device of the externally irradiation type in which the tube is spirally wound like this also can effectively irradiate the fluid having a low transmissivity with ultraviolet rays by making a tube diameter small and stirring the fluid by the spiral.

CITATION LIST

Patent Literature

Patent Literature 1 JP-A-2004-66045

SUMMARY OF THE INVENTION

However, according to Patent Literature 1, the following problem arises. Namely, when the fluid having a low ultraviolet ray transmissivity is irradiated with ultraviolet rays, it is preferable to make the wall thickness of the tube small in order to make the irradiation amount of the ultraviolet rays large. However, since the thin tube tends to be reduced in rigidity and pressure resistance, there is a probability that the tube vibrates due to an impact of a water hammer or the like generated by the circulation of the fluid, and the tube and the ultraviolet lamps are broken by the vibration.

In order to solve the problem like this, it is desirable to firmly support and fix the tube with an ultraviolet ray transmitting property which is spirally wound. For example, the method which fixes the tube by clamping the tube with belt-shaped support members that are disposed inside and outside the spiral, the method which puts a belt-shaped support member on the spiral of the tube and fixes the tube to the support member with a band and the like are conceivable. However, with these methods, irradiation of ultraviolet rays is shielded by the support member, and therefore, there arises a problem that the irradiation amount of ultraviolet rays with which the fluid is irradiated decreases.

The problem to be solved by the present invention is to support and fix a tube which is spirally wound and in which a fluid to be irradiated flows, and to increase an irradiation amount of ultraviolet rays with which the fluid is irradiated, in an ultraviolet irradiation device that is used for a fluid to be irradiated with a low ultraviolet ray transmissivity.

In order to solve the above described problem, an ultraviolet irradiation device of the present invention is characterized in that a tube having an ultraviolet ray transmitting property is spirally wound on an outer circumferential surface of a cylindrical body, a plurality of ultraviolet lamps are disposed around an axis of the cylindrical body apart from the tube, a casing that supports the cylindrical body and that encloses the plurality of ultraviolet lamps is provided, and a fluid flows in the tube and is irradiated with ultraviolet rays.

Namely, since the tube is supported and fixed onto the outer circumferential surface of the cylindrical body, a wall thickness of the tube which is a channel for a fluid to be irradiated is made small and an ultraviolet ray transmissivity of the tube can be increased. Further, the tube is strong against an inner pressure, and therefore, the wall thickness of the tube can be set so that the tube can withstand a required inner pressure. Meanwhile, the tube is supported by being wound on the cylindrical body, and therefore, the tube and the ultraviolet lamps which are disposed around the tube can be prevented from being broken by vibration of the tube.

Furthermore, since the tube is supported and fixed by spirally winding the tube on the outer circumferential surface of the cylindrical body, ultraviolet rays irradiated from the ultraviolet lamps are not shielded by a support member for the tube, by disposing the ultraviolet lamps outside a spiral of the tube, and therefore, an irradiation amount of ultraviolet rays is not reduced.

Namely, since the ultraviolet ray transmissivity of the tube is increased by making the wall thickness of the tube small by supporting and fixing the tube which is a channel for the fluid to be irradiated, and ultraviolet rays can be irradiated from outside the spiral of the tube without the ultraviolet rays being shielded, by disposing the cylindrical body inside the spiral of the tube, the irradiation amount of ultraviolet rays with which the fluid is irradiated can be increased. As a result, the ultraviolet irradiation device can be realized with a fluid having a low ultraviolet ray transmissivity as an irradiation target.

Further, it is preferable to reflect ultraviolet rays on the outer circumferential surface of the cylindrical body on which the spiral tube is wound. According thereto, ultraviolet rays that are transmitted through the tube and the fluid to be irradiated, and ultraviolet rays which pass through gaps in the tube are reflected on the outer circumferential surface of the cylindrical body, the fluid to be irradiated which flows in the tube is irradiated with the ultraviolet rays again, and therefore, the utilization efficiency of ultraviolet rays can be improved. In this case, the cylindrical body can be formed of metal having an ultraviolet ray reflecting property. Alternatively, on the outer circumferential surface of the cylindrical body formed from a resin or the like, a reflecting film can be formed from metal or the like that has an ultraviolet ray reflecting property. For example, when the cylindrical body and the reflecting film are formed from metal, it is preferable to use aluminum with a high reflectivity to ultraviolet rays, for example, aluminum with a purity equal to or higher than 90%.

Further, there is a fear that temperatures of the tube and the fluid to be irradiated in the tube are increased by irradiation of ultraviolet rays, and the tube and the fluid are deteriorated. In such a case, it is preferable to form the cylindrical body from a material with high thermal conductivity such as metal, and cool the tube and the fluid to be irradiated by causing a refrigerant to flow into the cylindrical body.

Meanwhile, when an irradiation amount of ultraviolet rays is measured, an ultraviolet illuminometer capable of measuring illuminances of a plurality of ultraviolet lamps is disposed in the support cylindrical body, and openings are formed in a cylinder wall of the support cylindrical body in positions corresponding to the plurality of ultraviolet lamps. According thereto, the illuminance of the ultraviolet rays that are transmitted through the tube and the fluid to be irradiated and are incident on an inside of the cylindrical body can be measured.

Further, the reflecting film is formed from aluminum or the like on the inner surface of the casing, and ultraviolet rays can be reflected in the casing. According thereto, ultraviolet rays which deviate from the tube are reflected on the reflecting film and are emitted onto the tube, and therefore, utilization efficiency of ultraviolet rays can be improved.

According to the present invention, in an ultraviolet irradiation device that is used for a fluid to be irradiated having a low ultraviolet ray transmissivity, the tube spirally wound in which the fluid to be irradiated flows can be supported and fixed, and the irradiation amount of ultraviolet rays with which the fluid is irradiated can be increased.

DETAILED DESCRIPTION OF THE PREFERRED EMBODIMENTS

Hereinafter, the present invention will be described based on embodiments.

Embodiment 1

As shown in FIGS. 1 to 5, an ultraviolet irradiation device of embodiment 1 is a so-called ultraviolet irradiation device of an external irradiation type in which ultraviolet lamps are disposed outside a tube that is a channel in which a fluid to be irradiated which is an irradiation target of ultraviolet rays flows, and ultraviolet rays are irradiated from outside the channel. In the ultraviolet irradiation device, a tube 3 having an ultraviolet ray transmitting property is spirally wound on an outer circumferential surface of a support pipe 5 which is a cylindrical body, and a plurality of ultraviolet lamps 7 are disposed around an axis of the support pipe 5 to be apart from the tube 3, so that the fluid to be irradiated which flows in the tube 3 is irradiated with ultraviolet rays from the ultraviolet lamps 7. The ultraviolet irradiation device is provided with an inner case 9 and an outer case 11, the plurality of ultraviolet lamps 7 are enclosed by the inner case 9 which supports the support pipe 5, and the inner case 9 is covered with the outer case 11.

Figure 1:
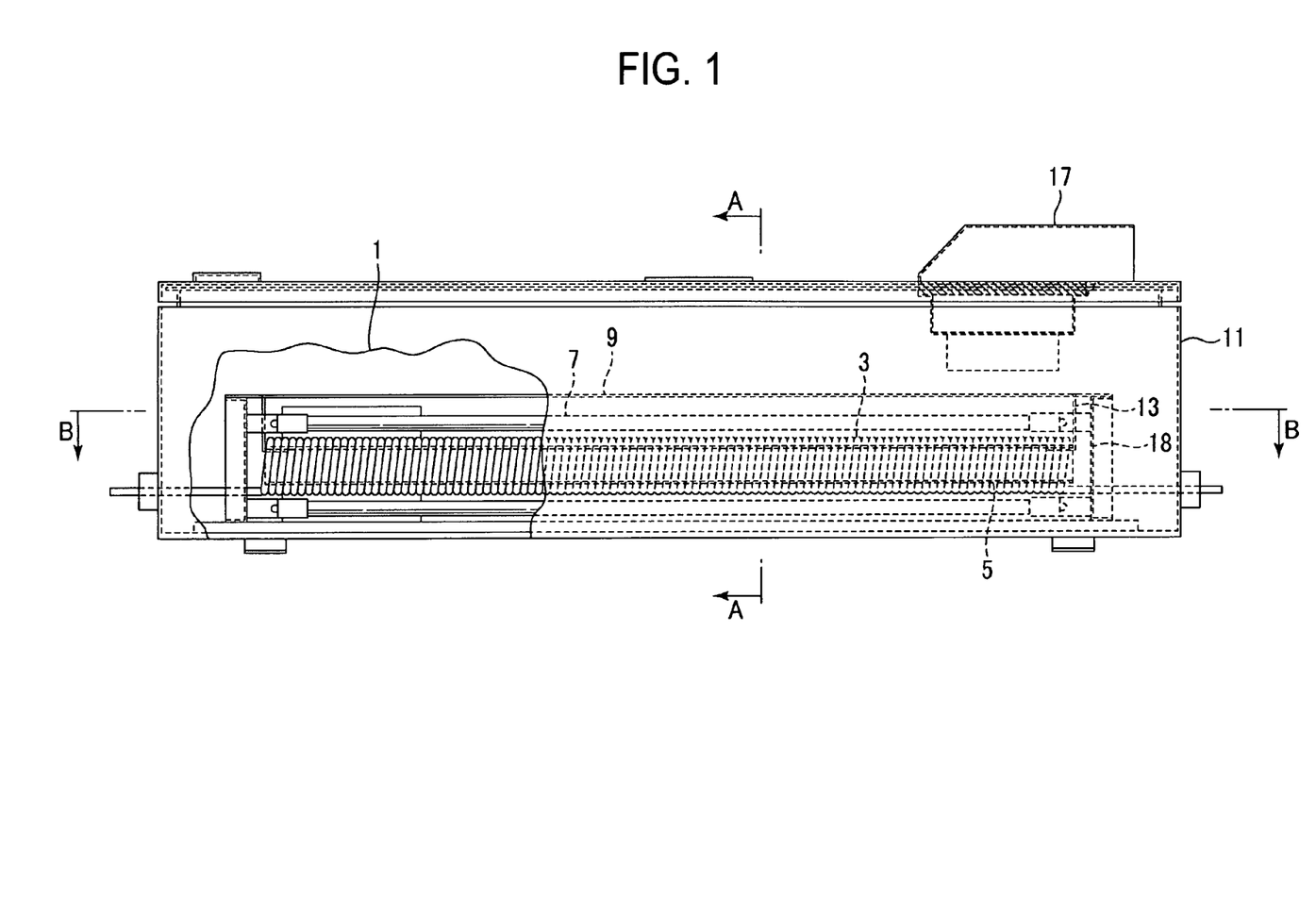
FIG. 1 is a side sectional view of an ultraviolet irradiation device of embodiment 1 of the present invention.
Figure 2:
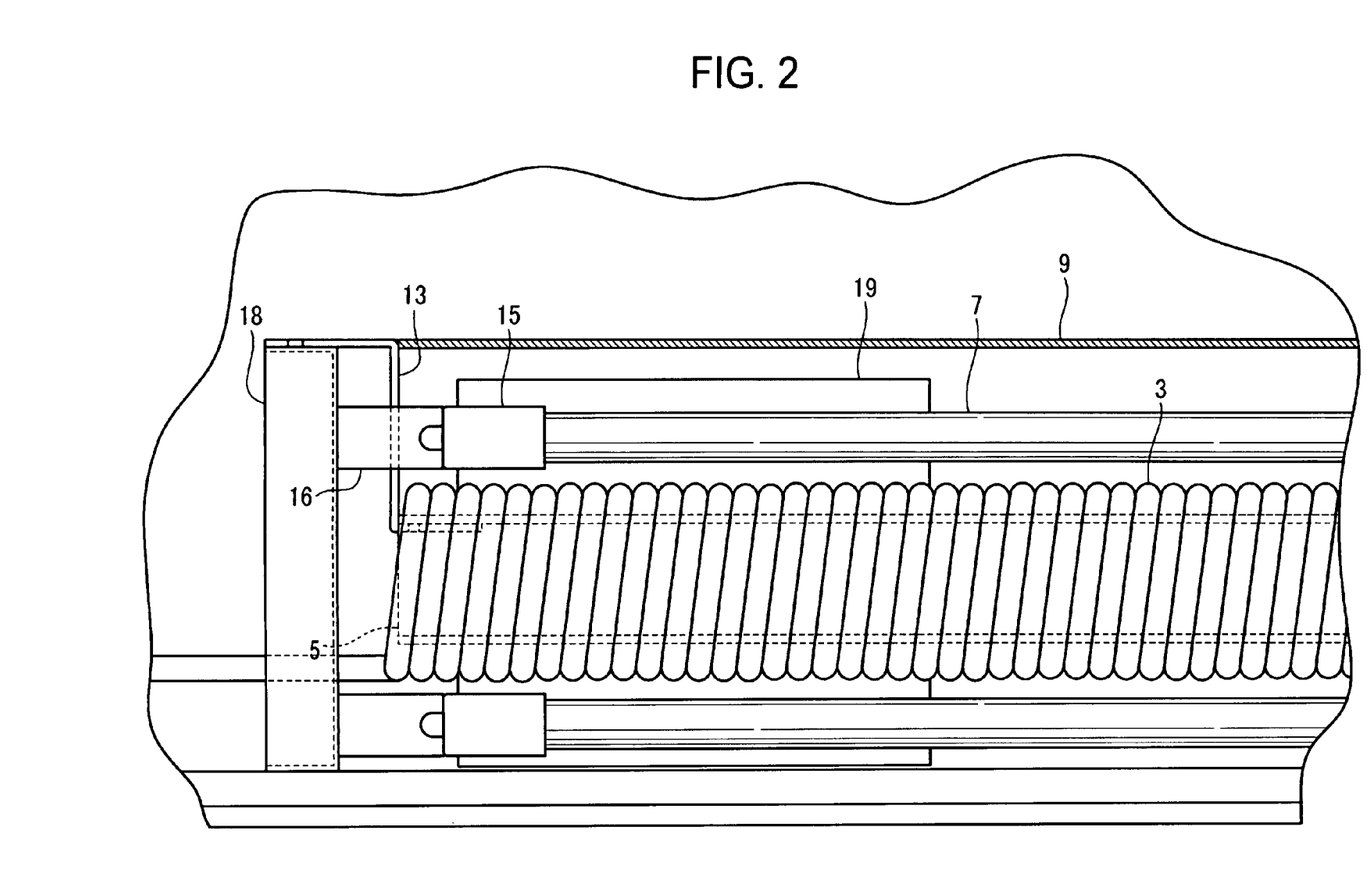
FIG. 2 is an enlarged view of a part in a frame 1 in FIG. 1.
Figure 3:
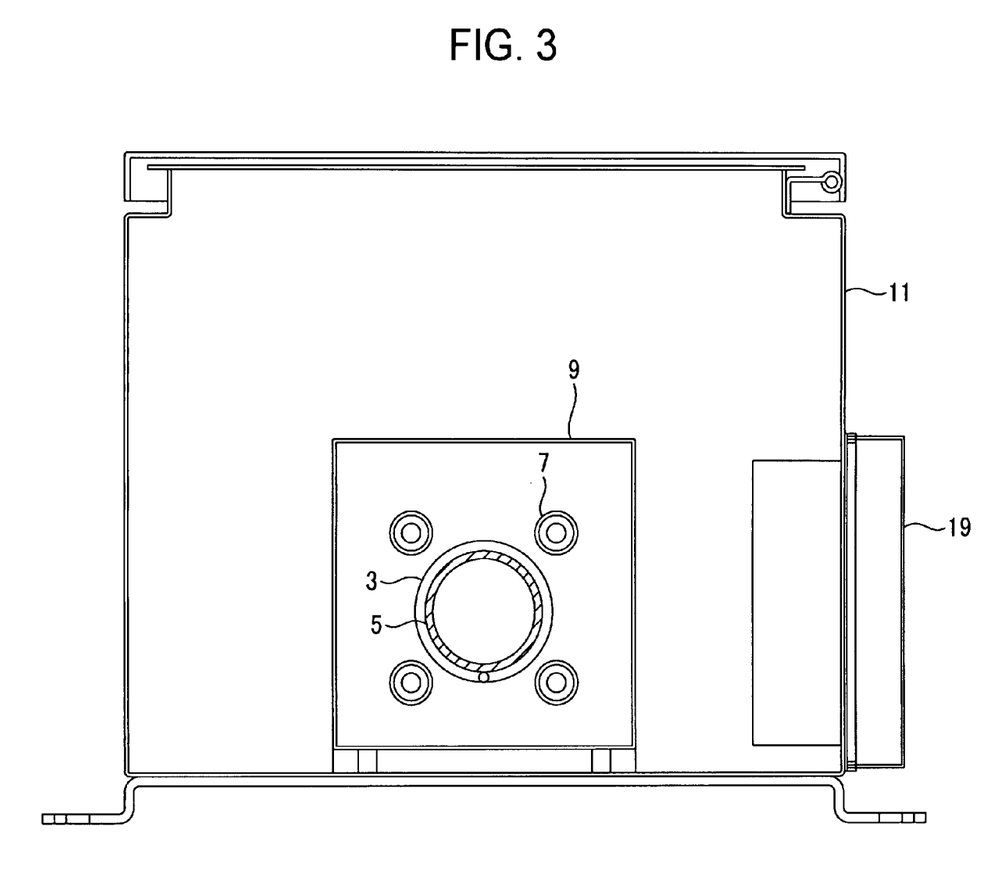
FIG. 3 is a sectional view taken along line A-A in FIG. 1.
Figure 4:
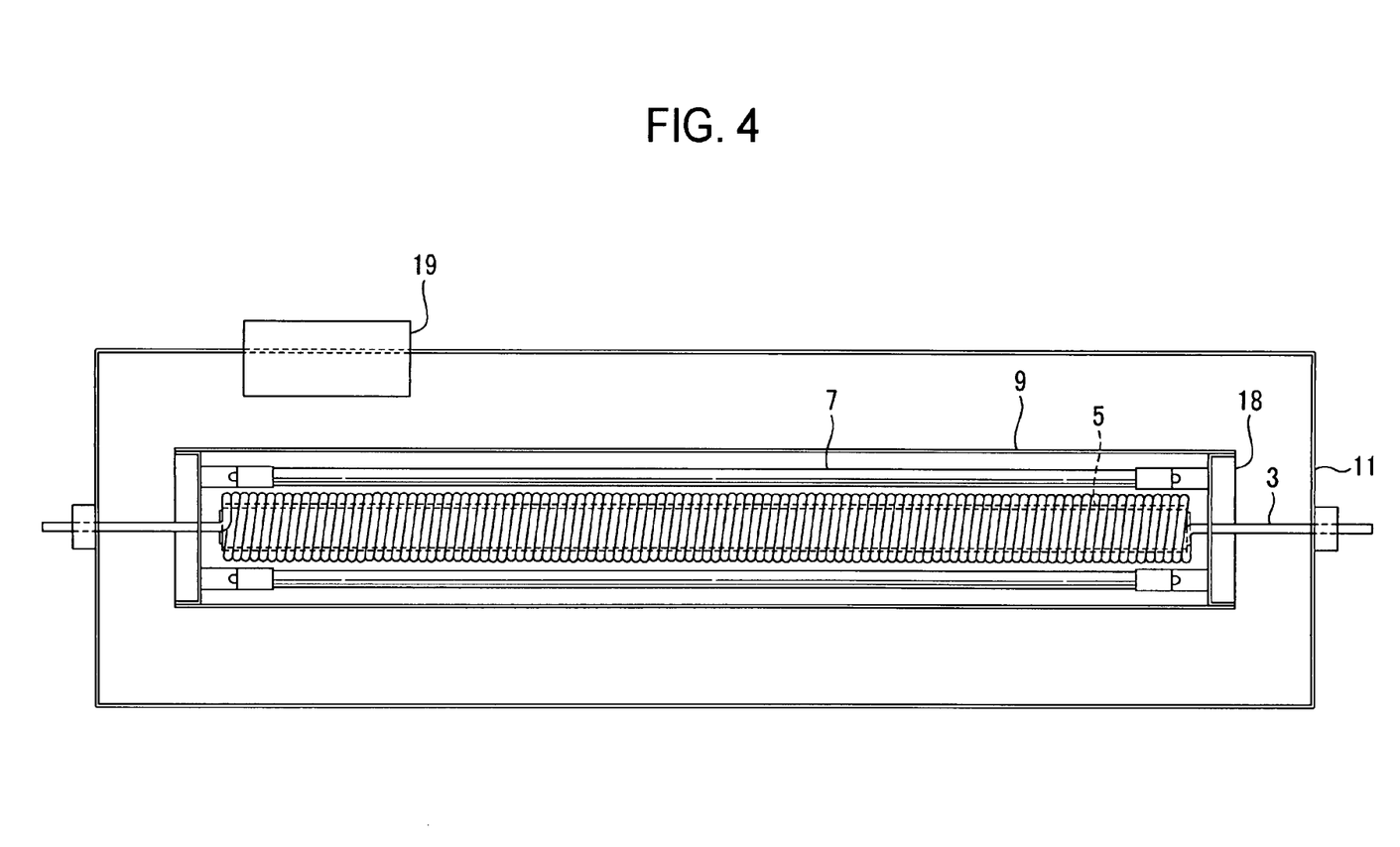
FIG. 4 is a sectional view taken along line B-B in FIG. 1.
Figure 5:
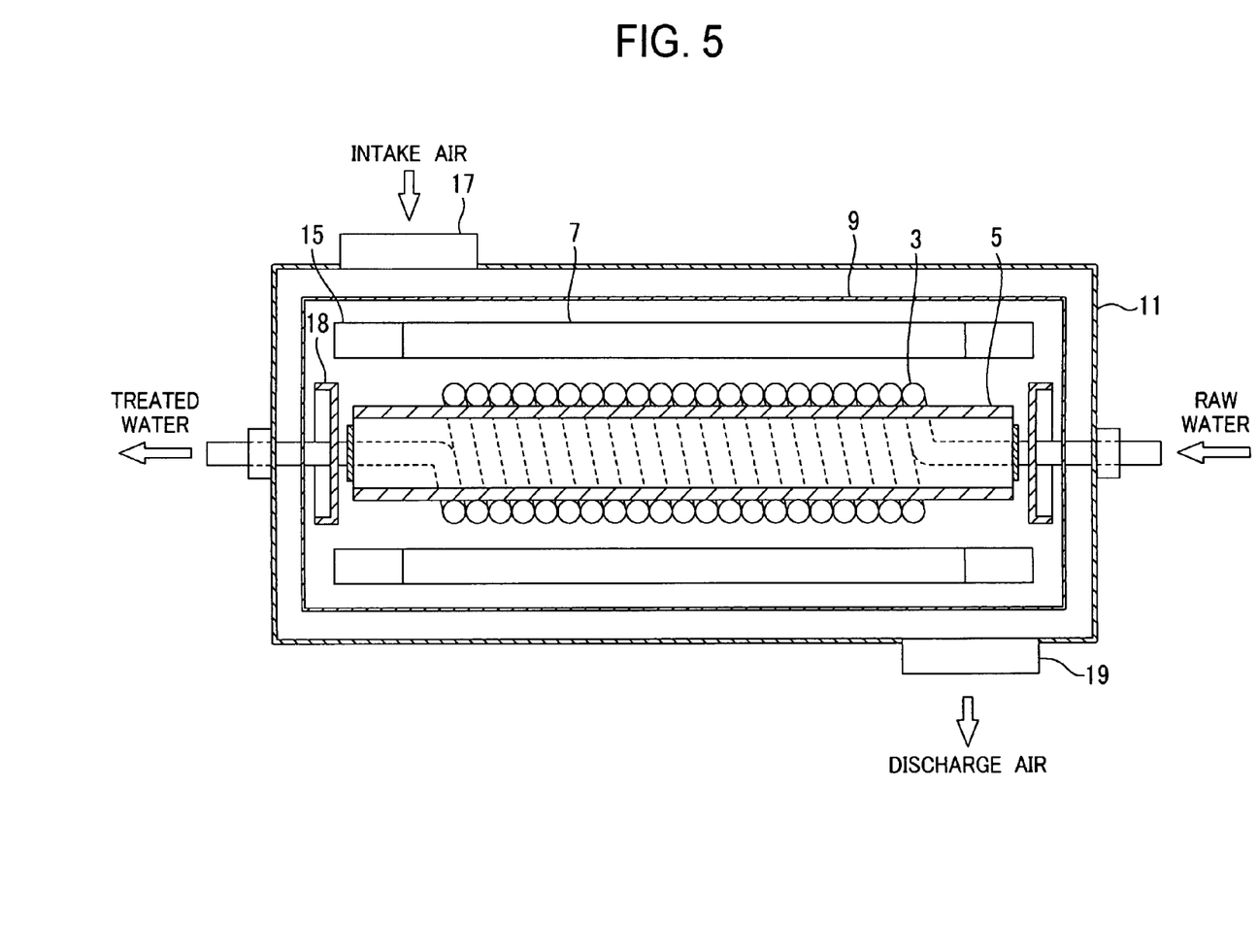
FIG. 5 is a conceptual diagram of the ultraviolet irradiation device of embodiment 1 of the present invention.

The tube 3 is a coil tube that is made by spirally winding a tube formed into a hollow cylinder from a fluorine resin, for example, and is a channel in which the fluid to be irradiated flows. One end side of the tube 3 is connected to inflow piping for the fluid to be irradiated, which is not illustrated, and the other end side is connected to outflow piping for the fluid to be irradiated. Note that as the fluorine resin used for the tube 3, for example, FEP (tetrafluoroethylene/hexafluoropropylene copolymer resin), PFA (tetrafluoroethylene), PTFE (polytetrafluoroethylene) and the like can be used.

The support pipe 5 is formed into a hollow cylinder from metal, for example, aluminum, and is supported and fixed with the tube 3 spirally wound on an outer circumferential surface. The support pipe 5 is disposed by being laid down, and is supported by the inner case 9 by a hook 13 that will be described later.

The plurality of ultraviolet lamps 7 are, for example, equidistantly disposed around the axis of the support pipe 5 apart from the tube 3. The respective ultraviolet lamps 7 are the ultraviolet lamps 7 each in a shape of a straight pipe with bases 15 formed at both ends, and are turned on or turned off by connecting the respective bases 15 to sockets 16.

The inner case 9 is formed into a box shape, and can accommodate the tube 3, the support pipe 5 and the ultraviolet lamps 7. The inner case 9 is formed of, for example, a reflecting plate of aluminum or the like that reflects ultraviolet rays. Ultraviolet rays that are irradiated by the plurality of ultraviolet lamps 7 are thereby repeatedly reflected into the inner case 9, and are emitted onto the tube 3. The inner case 9 is provided with a pair of hooks 13 that support the support pipe 5. The respective hooks 13 are each formed into an L-shape in which the hook 13 is suspended from an inner surface of the inner case 9 and folded in a horizontal direction. Horizontal portions of the respective hooks 13 are inserted into the support pipe 5 and support the support pipe 5. The support pipe 5 can be thereby supported in the inner case 9 with an extending direction of the support pipe 5 matched with the horizontal direction. Plate members 18 are supported at both ends of the inner case 9. In the plate member 18, an opening in which the tube 3 which is protruded from the end portion of the support pipe 5 is inserted and supported is formed. In a wall at an inner side of the plate member 18, a hole corresponding to a diameter of the tube 3 is formed so that the tube 3 can be pulled out of the wall at the inner side of the plate member 18.

The outer case 11 is formed into a box shape corresponding to the inner case 9 so as to cover the inner case 9. In a wall of the outer case 11, an intake port 17 through which outside air is taken in, and an exhaust port 19 through which air in the outer case 11 is discharged outside are formed. The intake port 17 is provided with a filter, and the exhaust port 19 is provided with a fan. By doing so, after the air outside the outer case 11 is cleaned through the filter, the air flows into the outer case 11 and cool an inside of the device, so that a temperature of the device is restrained from increasing.

An operation of the ultraviolet irradiation device of the present embodiment which is formed like this will be described. Note that here, the fluid to be irradiated having a low ultraviolet ray transmitting property is, for example, used in raw sewage treatment of livestock and is a supernatant liquid in an activated sludge tank, and a case of subjecting viruses in the supernatant liquid to inactivation treatment by irradiating the supernatant liquid with ultraviolet rays will be described as one example. Note that in order to make explanation understandable, the fluid to be irradiated before ultraviolet irradiation will be called raw water, and the fluid to be irradiated which is irradiated with a set amount of ultraviolet rays will be sometimes called treated water.

In a state in which the plurality of ultraviolet lamps 7 are lit, the supernatant liquid (raw water) flows into the tube 3 via the inflow piping from the activated sludge tank not illustrated. The raw water which flows into the tube 3 flows into the inner case 9 from the outer case 11, and is guided into the tube 3 which is spirally wound. The raw water which flows in the spiral tube 3 is irradiated with ultraviolet rays by the plurality of ultraviolet lamps 7. At this time, if a wall thickness of the tube 3 is formed to be small within a range in which the tube 3 can withstand inner pressure in order to increase the ultraviolet ray transmissivity of the tube 3, there is the fear that the tube 3 vibrates due to impact by passage of the raw water, and the tube 3 is damaged. However, in the present embodiment, the tube 3 is fixed by being supported by the support pipe 5 so as to be able to withstand the impact due to passage of the raw water, and therefore, the tube 3 does not move. Since as a result, vibration of the tube 3 which occurs due to passage of the raw water can be restrained, the tube 3 can be prevented from being damaged, and damage of the ultraviolet lamps 7 by the tube 3 vibrating and colliding with the ultraviolet lamps 7 can be prevented.

The raw water which flows through the spiral part of the tube 3 flows while being stirred along the spiral, and therefore, the supernatant liquid having a low transmissivity in the activated sludge tank can be uniformly irradiated with ultraviolet rays. The viruses in the raw water can be thereby subjected to inactivation treatment. The treated water which goes through the inactivation treatment by irradiation of ultraviolet rays flows out to an outflow piping from the outer case 11, is properly treated if necessary, and is discharged to a river or the like.

Meanwhile, the ultraviolet rays which are transmitted through the tube 3 and the raw water, and pass through gaps in the tube 3 are reflected on the outer circumferential surface of the support pipe 5 of aluminum. By the reflection, the ultraviolet rays can be irradiated toward the raw water in the tube 3 again, and therefore, utilization efficiency of ultraviolet rays can be improved. Further, by reflecting the ultraviolet rays which hit the support pipe 5, heating of the support pipe 5 by ultraviolet rays can be restrained, and deterioration of the tube 3 and the raw water caused by the support pipe 5 being heated and the tube 3 being heated can be reduced.

Further, the ultraviolet rays which travels in the direction to be away from the tube 3 are reflected inside the inner case 9 which is formed of the reflecting plate and can be emitted onto the raw water in the tube 3, and therefore, the ultraviolet rays which are emitted onto the raw water can be increased.

As above, according to the ultraviolet irradiation device of the present embodiment, the channel for the raw water is formed of the tube 3 which is strong to the inner pressure, and therefore, the wall thickness of the tube can be set to be thin within the range in which the tube can withstand the inner pressure by the raw water. Since the tube 3 is fixed by being supported by the support pipe 5, the tube 3 can be prevented from vibrating due to passage of the raw water, damage to the tube 3 and the ultraviolet lamps 7 due to the vibration of the tube 3 can be restrained. The ultraviolet ray transmissivity of the tube 3 can be thereby increased by making the wall thickness of the tube 3 small, and therefore, the ultraviolet irradiation amount to the raw water which flows in the tube 3 can be increased.

Furthermore, the tube is supported and fixed by spirally winding the tube 3 on the outer circumferential surface of the support pipe 5, and therefore, the ultraviolet lamps 7 are disposed outside the spiral of the tube 3, whereby the ultraviolet rays which are irradiated by the ultraviolet lamps 7 are not shielded by the support pipe 5 which is the support member for the tube 3, and therefore, the irradiation amount of the ultraviolet rays is not reduced.

Namely, since the ultraviolet ray transmissivity of the tube can be increased by making the wall thickness of the tube 3 small by supporting and fixing the tube 3 which is the channel for the raw water, and by disposing the support pipe 5 inside the spiral of the tube 3, ultraviolet rays can be irradiated from outside the spiral of the tube 3 without the ultraviolet rays being shielded, the irradiation amount of the ultraviolet rays with which the raw water is irradiated can be increased. A fluid having a low ultraviolet ray transmissivity, for example, a fluid having an ultraviolet ray transmissivity in a liquid layer thickness of 1 cm, equal to or lower than 10% can be thereby made an irradiation target.

Further, since the tube 3 is fixed, it does not happen that the tube 3 moves to collide with the ultraviolet lamps 7 whereby the ultraviolet lamps 7 are broken. Since, as a result, the ultraviolet lamps 7 can be disposed close to the tube 3, the irradiation amount of ultraviolet rays can be increased, and the fluid to be irradiated with a low ultraviolet ray transmissivity can be reliably irradiated with ultraviolet rays.

Further, if the spiral tube 3 is laid in the horizontal direction without being fixed, there is the fear that the tube 3 hangs down to be broken. However, in the present embodiment, the spiral tube 3 is fixed to the support pipe 5, and therefore, even when the spiral tube 3 is disposed by being laid in the horizontal direction, the tube 3 does not hang down. Therefore, it can be selected whether the spiral tube 3 is raised in a vertical direction, or laid in the horizontal direction, and therefore, the degrees of freedom of the device design and the installation place can be improved.

Note that the present embodiment illustrates the treatment of inactivating the viruses in the supernatant liquid with the supernatant liquid in the activated sludge tank adopted as the fluid having a low ultraviolet ray transmissivity, but the use purpose of the ultraviolet irradiation device of the present embodiment is not limited to this. For example, the ultraviolet irradiation device can be used in, for example, sterilization of bacteria included in juice of a fruit, sterilization of molasses which is generated when sugar is produced, decomposition of harmful substances in industrial waste water, or the like.

Further, the tube 3 which is the fluid channel can be formed from quartz glass in place of a fluorine resin, but quartz glass has lower tensile strength as compared with a fluorine resin, and is easily broken by the inner pressure due to passage of the fluid, and therefore, use of a fluorine resin is preferable.

Further, in the present embodiment, in order to reflect ultraviolet rays on the outer circumferential surface of the support pipe 5, the entire support pipe 5 is formed of aluminum, but forming the support pipe 5 of a resin and forming a film that reflects ultraviolet rays, of aluminum or the like on the outer circumferential surface and the like can be properly selected. Further, when the transmissivity of the fluid to be irradiated is low, and ultraviolet rays do not reach the outer circumferential surface of the support pipe 5, a material which does not reflect ultraviolet rays can be used for the outer circumferential surface of the support pipe 5.

Further, in the present embodiment, in order to irradiate the fluid to be irradiated with ultraviolet rays which travel in the direction to be away from the fluid to be irradiated, the inner case 9 is formed of the reflecting plate of aluminum, but forming a reflecting film that reflects ultraviolet rays on the inner surface of the inner case 9 or the like can be adopted, if only ultraviolet rays can be reflected in the inner case 9.

Further, a groove corresponding to an outer shape of the tube 3 can be formed on the outer circumferential surface of the support pipe 5. According to this, the tube 3 is wound along the groove, whereby support and fixation of the tube 3 becomes much firmer. Further, positioning of the tube 3 becomes easy, and operability in manufacture or the like can be improved.

Embodiment 2

Figure 6:
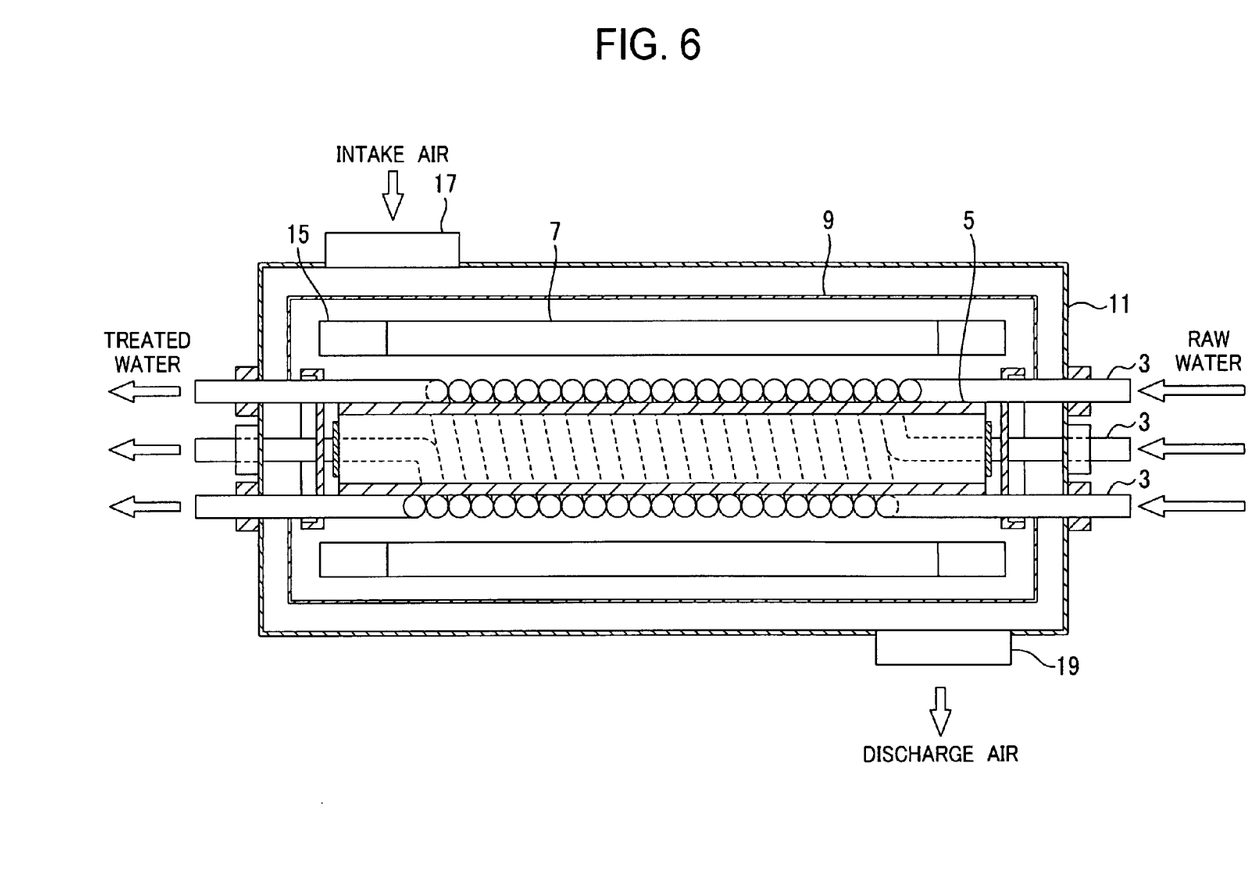
FIG. 6 is a conceptual diagram of an ultraviolet irradiation device of embodiment 2 of the present invention.

FIG. 6 shows a conceptual diagram of a section of an ultraviolet irradiation device of embodiment 2. A point in which embodiment 2 differs from embodiment 1 is a point in which a plurality of tubes 3, for example, three tubes 3 are spirally wound on the outer circumferential surface of the support pipe 5 so as not to overlay one another. Namely, embodiment 2 differs from embodiment 1 in a point in which a channel sectional area of a fluid to be irradiated is made three times as large as that of embodiment 1. The other components are the same as those in embodiment 1, and therefore, sill be assigned with the same reference signs, and explanation thereof will be omitted.

According to this, the sectional area of the channel in which the fluid to be irradiated flows is increased by increasing the number of tubes 3, and therefore, the flow amount of the fluid to be irradiated can be increased without increasing pressure loss. Note that the number of tubes 3 can be properly selected based on a treatment amount of the fluid to be irradiated, the transmissivity of the fluid to be irradiated and the like.

Embodiment 3

Figure 7:
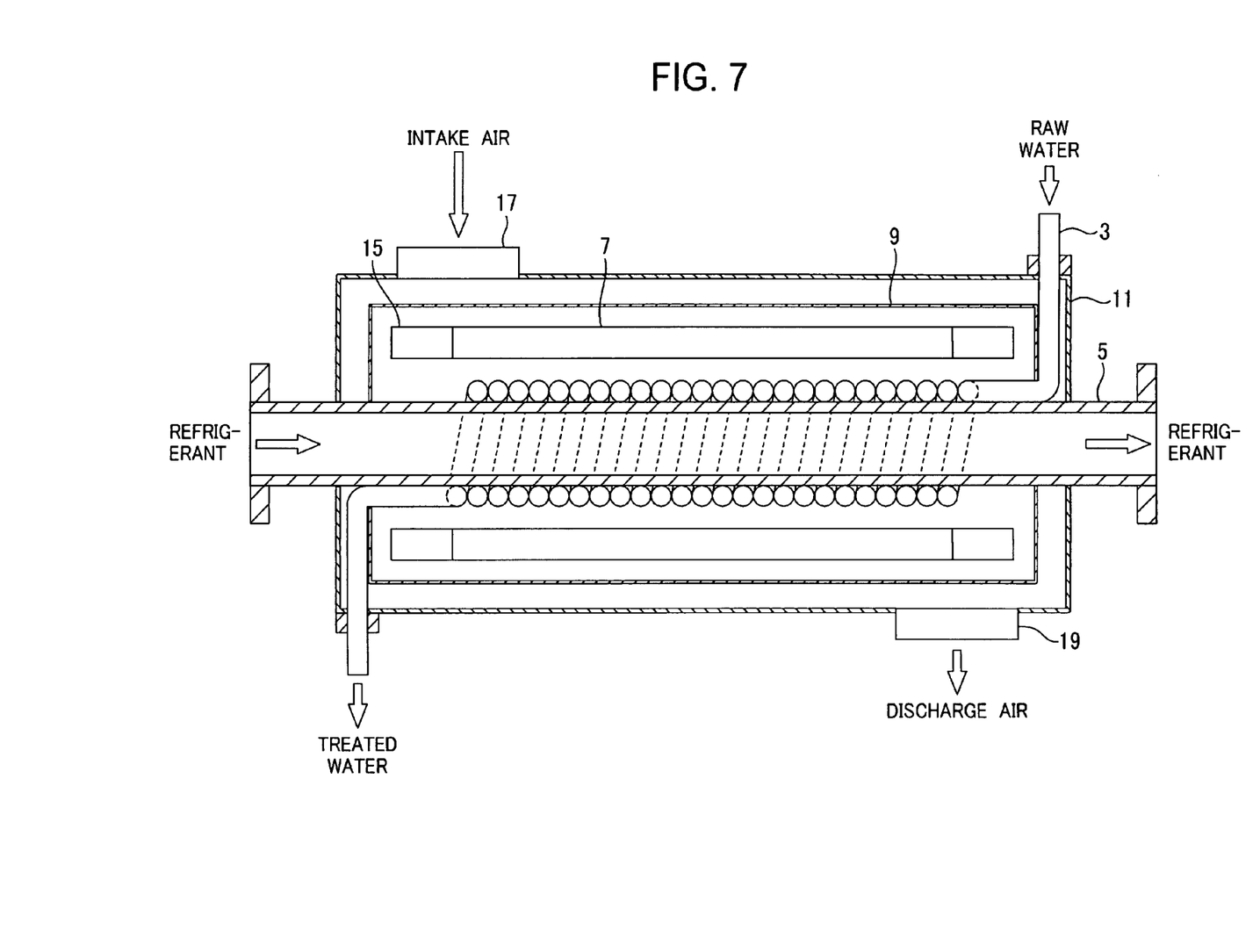
FIG. 7 is a conceptual diagram of an ultraviolet irradiation device of embodiment 3 of the present invention.

FIG. 7 shows a conceptual diagram of an ultraviolet treatment device of embodiment 3. A point in which embodiment 3 differs from embodiment 1 is a point in which a refrigerant flows in the support pipe 5 to cool a fluid to be irradiated. The other components are the same as those in embodiment 1, and therefore will be assigned with the same reference signs, and explanation thereof will be omitted.

The support pipe 5 is formed from metal with a high thermal conductivity. Both ends of the support pipe 5 are inserted into and supported at openings that are formed in the inner case 9 and the outer case 11, and are drawn to outside from the outer case 11. Of end portions of the support pipe 5, to an end portion at an outflow side of treated water, inflow piping for the refrigerant is connected, and to an end portion at an inflow side of raw water, outflow piping for the refrigerant is connected. The refrigerant thereby flows in the support pipe 5 to face an outflow direction of the fluid to be irradiated.

Here, a characteristic operation of the present embodiment will be described. While the fluid to be irradiated is flowing in the spiral tube 3, a temperature of the fluid to be irradiated increases by irradiation of ultraviolet rays. Therefore, it is difficult to irradiate the fluid to be irradiated which deteriorates by temperature increase with ultraviolet rays. Thus, in the present embodiment, the support pipe 5 on which the tube 3 is spirally wound is formed of metal or the like with a high thermal conductivity, and the refrigerant is caused flow therein, whereby the fluid to be irradiated in the tube 3 is cooled via the support pipe 5.

According to this, the fluid to be irradiated which flows in the tube 3 can be cooled with the refrigerant which flows in the support pipe 5, and therefore, increase in the temperature of the fluid to be irradiated by irradiation of ultraviolet rays can be restrained. As a result, the fluid to be irradiated which contains a substance which is deteriorated by temperature increase can be also irradiated with ultraviolet rays. Note that as the metal forming the support pipe 5, use of aluminum with a high reflectivity to ultraviolet rays is preferable. According to this, the fluid to be irradiated can be cooled, while the ultraviolet rays which hit the outer circumferential surface of the support pipe 5 can be reflected and emitted onto the fluid to be irradiated, and therefore, the amount of effective ultraviolet rays which are emitted onto the fluid to be irradiated can be increased.

Embodiment 4

Figure 8:
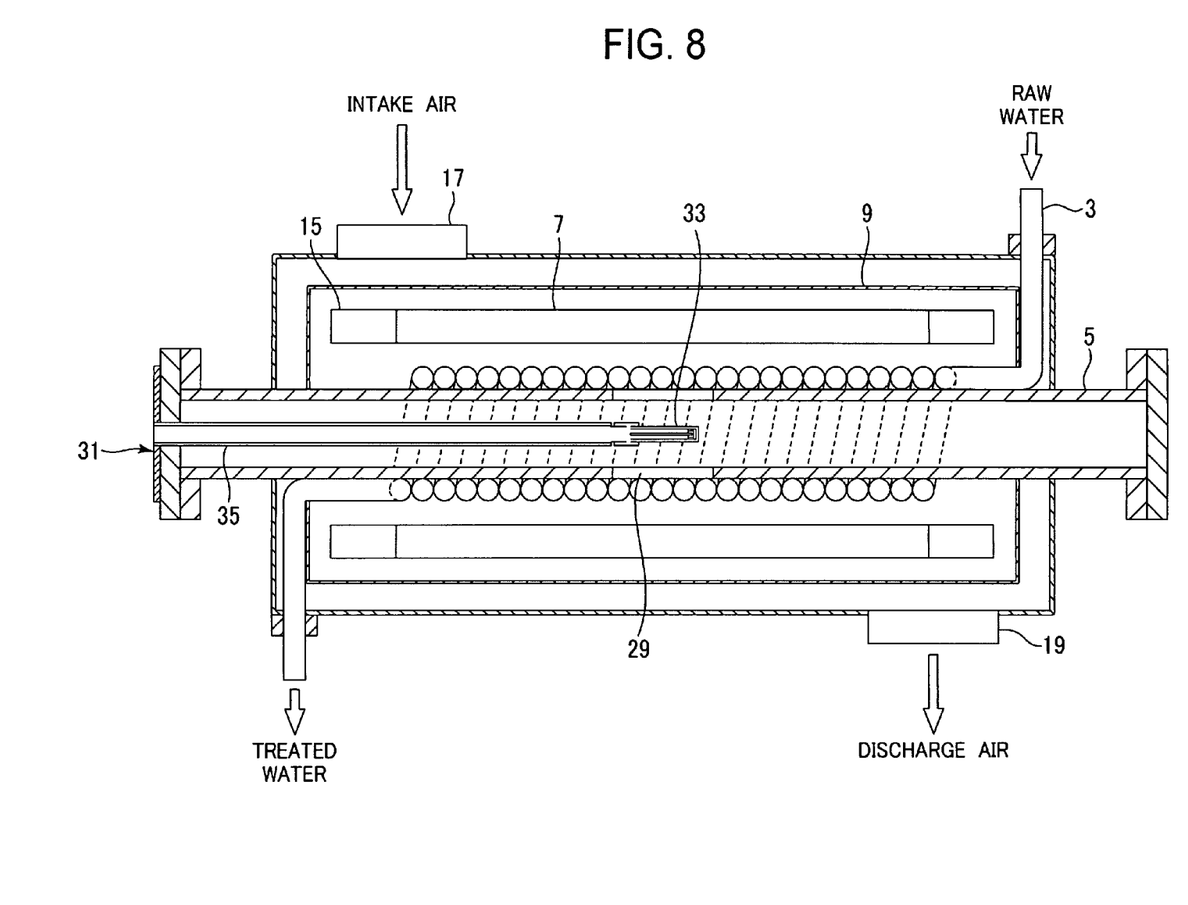
FIG. 8 is a conceptual diagram of an ultraviolet irradiation device of embodiment 4 of the present invention.

FIG. 8 shows a conceptual diagram of an ultraviolet irradiation device of embodiment 4. A point in which embodiment 4 differs from embodiment 1 is a point in which an illuminometer 31 that measures illuminances of a plurality of ultraviolet lamps 7 is disposed in the support pipe 5, openings corresponding to the respective ultraviolet lamps 7 are formed in a wall surface of the support pipe 5, which faces the illuminometer 31, and ultraviolet illuminances of the plurality of ultraviolet lamps 7 are measured. The other components are the same as those in embodiment 1, and therefore, will be assigned with the same reference sings, and explanation thereof will be omitted.

Both ends of the support pipe 5 are inserted in and support at the openings formed in the inner case 9 and the outer case 11, and are drawn out to outside from the outer case 11. Slits 29 corresponding to the respective ultraviolet lamps 7 are formed in a pipe wall of the support pipe 5. The slits 29 are formed along an extending direction of the support pipe 5, and are opened toward the respective ultraviolet lamps 7. The illuminometer 31 which is inserted and supported in the support pipe 5 includes, for example, a columnar sensor 33, and a support rod 35 that supports the sensor 33. The sensor 33 can measure ultraviolet rays throughout an entire circumference. In the support rod 35, a transmission medium that transmits the illuminance of ultraviolet rays received by the sensor 33 to outside is accommodated, for example. The illuminometer 31 is inserted into the support pipe 5, and the support rod 35 is mounted to the support pipe 5 in such a manner that the sensor 33 is located at positions of the slits 29. The ultraviolet rays which are transmitted through the tube 3 are thereby incident on the inside of the support pipe 5 from the respective slits 29 and are received by the sensor 33, and therefore, the illuminance of the ultraviolet rays can be measured.

According to this, the illuminance of the ultraviolet rays can be measured, and therefore, if there is the ultraviolet lamp 7 which remains off or is reduced in ultraviolet output due to a fault or the like, a measured value of the illuminance of ultraviolet rays reduces, and the ultraviolet lamp 7 can be found. Accordingly, by properly performing replacement or the like of the ultraviolet lamp 7 with ultraviolet output reduced, insufficiency of irradiation amount of ultraviolet rays due to a fault or the like can be prevented.

Further, the ultraviolet rays which are received by the sensor 33 are the ultraviolet rays which are transmitted through the fluid to be irradiated, and therefore, if the ultraviolet ray transmissivity of the fluid to be irradiated is reduced for some reason, a detected illuminance of the illuminometer 31 reduces. Therefore, a variation of the ultraviolet ray transmissivity of the fluid to be irradiated can be detected. Thereby, when the ultraviolet ray transmissivity is reduced, a measure to increase output of the ultraviolet lamp 7 or the like is taken, whereby a set amount of ultraviolet ray can be reliably emitted onto the fluid to be irradiated.

Note that the illuminometer 31 of the present embodiment receives the ultraviolet rays that are transmitted through the fluid to be irradiated, but the illuminometer 31 can be configured to receive ultraviolet rays that are not transmitted through the fluid to be irradiated. For example, the tube 3 is spirally wound on the support pipe 5 in such a manner as to avoid the respective slits 29 of the support pipe 5, whereby the ultraviolet rays irradiated from the ultraviolet lamps 7 are directly incident on the support pipe 5 from the respective slits 29. In this case, plate members that protrude from the outer circumferential surface of the support pipe 5 are formed at edges of the respective slits 29, and by the plate members, the tube 3 can be configured not to close the respective slits. According to this, even when the fluid to be irradiated having a low ultraviolet ray transmissivity is irradiated with ultraviolet rays, the ultraviolet rays can be caused to be incident on the inside of the support pipe 5, and therefore, the illuminance of the ultraviolet rays can be measured.

Further, when the refrigerant flows in the support pipe 5 as in embodiment 3, the illuminometer 31 cannot be disposed in the support pipe 5, and therefore, in this case, the illuminometer can be installed outside the support pipe 5.

REFERENCE SIGNS LIST

3 Tube, 5 Support pipe, 7 Ultraviolet lamp, 9 Inner case, 11 Outer case, 13 Hook, 29 Slit, 31 Illuminometer, 33 Sensor, 35 Rod

What is claimed is:

1. An ultraviolet irradiation device, comprising:
   a tube comprised of a fluorine resin and having an ultraviolet ray transmitting property, the tube being spirally wound on an outer circumferential surface of a cylindrical support pipe;
   a plurality of ultraviolet lamps disposed around an axis of the cylindrical support pipe apart from the tube; and
   a casing that supports the cylindrical support pipe and that encloses the plurality of ultraviolet lamps,
   wherein a fluid flows in the tube and is irradiated with ultraviolet rays.

2. The ultraviolet irradiation device according to claim 1, wherein the cylindrical support pipe is formed of metal.

3. The ultraviolet irradiation device according to claim 1, wherein at least the outer circumferential surface of the cylindrical support pipe is formed of aluminum.

4. The ultraviolet irradiation device according to claim 2, wherein at least the outer circumferential surface of the cylindrical support pipe is formed of aluminum.

5. The ultraviolet irradiation device according to claim 1, wherein a refrigerant flows in the cylindrical support pipe.

6. The ultraviolet irradiation device according to claim 1, wherein an ultraviolet illuminometer that measures illuminances of the plurality of ultraviolet lamps are disposed in the cylindrical support pipe, and openings corresponding to the plurality of ultraviolet lamps are formed on a surface of the cylindrical support pipe.

7. The ultraviolet irradiation device according to claim 1, wherein a reflecting surface that reflects ultraviolet rays is formed on an inner surface of the casing.

8. The ultraviolet irradiation device according to claim 2, wherein a reflecting surface that reflects ultraviolet rays is formed on an inner surface of the casing.

9. The ultraviolet irradiation device according to claim 3, wherein a reflecting surface that reflects ultraviolet rays is formed on an inner surface of the casing.

10. The ultraviolet irradiation device according to claim 4, wherein a reflecting surface that reflects ultraviolet rays is formed on an inner surface of the casing.

11. The ultraviolet irradiation device according to claim 5, wherein a reflecting surface that reflects ultraviolet rays is formed on an inner surface of the casing.

12. The ultraviolet irradiation device according to claim 6, wherein a reflecting surface that reflects ultraviolet rays is formed on an inner surface of the casing.

* * * * *